United States Patent
Warring et al.

(10) Patent No.: US 6,832,663 B2
(45) Date of Patent: Dec. 21, 2004

(54) EAR COUPLER

(75) Inventors: Jessica Ash Warring, San Carlos, CA (US); Alfred Christian Walton, Belmont, CA (US)

(73) Assignee: Natus Medical Inc., San Carlos, CA (US)

( * ) Notice: Subject to any disclaimer, the term of this patent is extended or adjusted under 35 U.S.C. 154(b) by 0 days.

(21) Appl. No.: 09/941,132

(22) Filed: Aug. 27, 2001

(65) Prior Publication Data

US 2003/0037988 A1 Feb. 27, 2003

(51) Int. Cl.⁷ .............................................. H04R 25/00
(52) U.S. Cl. ...................................................... 181/129
(58) Field of Search ................................ 181/129, 130, 181/132, 134, 135, 136, 137

(56) References Cited

U.S. PATENT DOCUMENTS

| | | | |
|---|---|---|---|
| 4,375,016 A | * | 2/1983 | Harada ........................ 181/135 |
| 4,930,520 A | | 6/1990 | Liverani |
| 5,440,082 A | * | 8/1995 | Claes .......................... 181/135 |
| 5,826,582 A | | 10/1998 | Sheehan et al. |
| 6,151,717 A | * | 11/2000 | Lindgren et al. ............... 2/209 |
| 6,386,314 B1 | * | 5/2002 | Sheehan et al. ............ 181/129 |
| 6,427,686 B2 | * | 8/2002 | Augustine et al. ..... 128/200.26 |

FOREIGN PATENT DOCUMENTS

GB          2010640 A        6/1979

\* cited by examiner

*Primary Examiner*—Kimberly Lockett
(74) *Attorney, Agent, or Firm*—Daniel P. Maguire

(57) ABSTRACT

A one-piece, transparent flexible ear coupler for use with hearing evaluation is disclosed. It includes an annular side wall and a bottom wall forming an acoustic chamber. A flexible adhesive-backed flange is disposed on the periphery of the ear coupler. The flange attaches to the subject's head, firmly holding the ear coupler in place over the ear. The annular side wall has a port for the placement of a transducer assembly, and also has ribs to help lock the transducer assembly in place. The transducer assembly can be placed in an up or down position, and can be switched between positions while the coupler is attached to the subject's head. The ear coupler advantageously conforms to the subject's head, thereby minimizing the likelihood that the ear coupler will become detached during testing. The coupler can be inexpensively manufactured, since its one-piece design allows the use of relatively low-cost processes such as injection molding and thermoforming.

28 Claims, 6 Drawing Sheets

EAR COUPLER

BACKGROUND OF THE INVENTION

1. Field of the Invention

The present invention relates to ear couplers or earphones that cover the ear to create a desired acoustic environment.

2. Background of the Invention

It is inherently difficult to determine hearing impairment in infants, since they cannot participate in traditional hearing tests which require subjects to indicate whether they can hear various sounds. However, if hearing impairment is not detected until the infant grows into a toddler or child, then the potential for long-term disability increases, since the child's language skills will have developed before remedial measures have been undertaken. The optimal time to screen for hearing impairment is immediately after birth, both because early detection allows for early treatment, and because parents often fail to bring their children in for later appointments.

Devices and methods have been developed to evaluate infant hearing by subjecting an infant to an aural stimulus, and then measuring the electroencephalographic or otoacoustic response to that stimulus. These devices and methods depend on the creation of the proper acoustic environment about the subject's ear, so that ambient noise does not interfere with the hearing evaluation, and so that the stimulus has the appropriate duration, amplitude, and frequency content.

To create the desired acoustic environment, earphones or ear couplers have been used. Information relevant to previous ear couplers can be found in U.S. Pat. Nos. 5,826,582, 4,930,520, and in U.S. patent application Ser. No. 09/395,799. Although many of these devices have worked well, they can sometimes become detached from the subject's head, because of the variable and irregular surfaces surrounding the ear, and because infants tend to move during testing. Additionally, with previous ear couplers, the assembly that houses the stimulus-producing transducer tends to tug the ear coupler away from the ear. Existing ear couplers are also relatively expensive to manufacture, in part because they require production or assembly of more than one part.

It is therefore desirable to construct an ear coupler that is better able to remain attached to the subject's head, and that is not subject to being tugged off the head by forces acting on the transducer housing. It is also desirable to design a one-piece ear coupler that can be inexpensively manufactured by injection molding or other suitable processes.

BRIEF SUMMARY OF THE INVENTION

The present invention is a transparent one-piece ear coupler, with an internal chamber that creates a tuned acoustic environment about the subject's ear, with a port to accommodate a transducer, and with a flange positioned around the periphery of the coupler to attach the coupler to the subject's head.

Other features of the preferred embodiment of the present invention include a tab to facilitate removal of the ear coupler, and a mark or target on the coupler to help ensure proper alignment over the subject's ear. The coupler is generally D-shaped, and is designed so as to fit on either ear. Preferably, the coupler is made of transparent Rimflex® thermoplastic elastomer, although other flexible, transparent materials could be used. The bottom wall of the coupler contains waffle-shaped or other surface features, which add rigidity and create the desired acoustic characteristics of the chamber.

The exterior wall of the coupler is ribbed to provide means to securely lock in place the housing that contains the transducer. The side of the flange in contact with the skin contains hydrogel or another adhesive substance to stick to the subject's head. The interior surface of the flange may also contain waffle-shaped or other surface features for improved adhesion of the hydrogel to the Rimflex®, although no such extrusions are provided in the preferred embodiment of this invention. The walls of the coupler are of sufficient thickness to resist crushing, and to provide the desired acoustic environment about the subject's ear.

The housing that contains the transducer, known as an acoustic transducer assembly (ATA), securely and positively fits into the port that enters into the internal chamber. The ATA latches onto ribs on the sides of the coupler, and can be rotated up or down while in use, so that the length of the ATA can placed either above or below the center of the coupler.

Before being attached to the subject's head, the ear couplers are attached to release paper. Preferably, the adhesive that secures the ear couplers to the release paper (and to the subject's head) is a hydrogel, which can be selectively applied only to the flange of the ear coupler during manufacture, thereby minimizing waste. There are holes in the release paper, centered over the chamber of the ear coupler, to help the user hold the coupler while the ATA is being inserted.

In operation, the ATA is inserted into the port, and the ear coupler is removed from the release paper and placed on the subject's ear. The adhesive on the flange sticks to the subject's head, and because of the unique features of the invention as disclosed herein, the ear coupler will tend to stay affixed to the infant's head, even if he or she moves during testing. The tab helps remove the ear coupler from the release paper, and helps remove it from the subject's head when the testing is complete.

DETAILED DESCRIPTION

Figure 1:
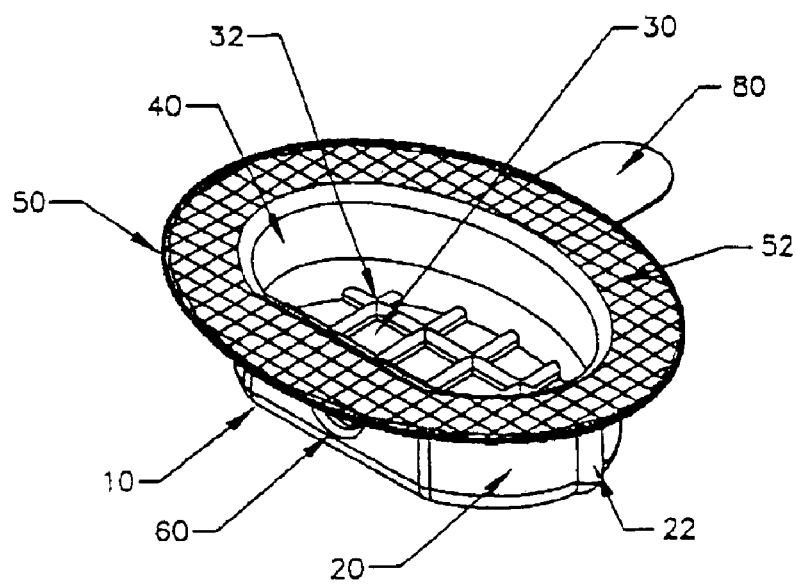
FIG. 1 is an elevated perspective view of the ear coupler in accordance with a preferred embodiment of the present invention.
Figure 2:
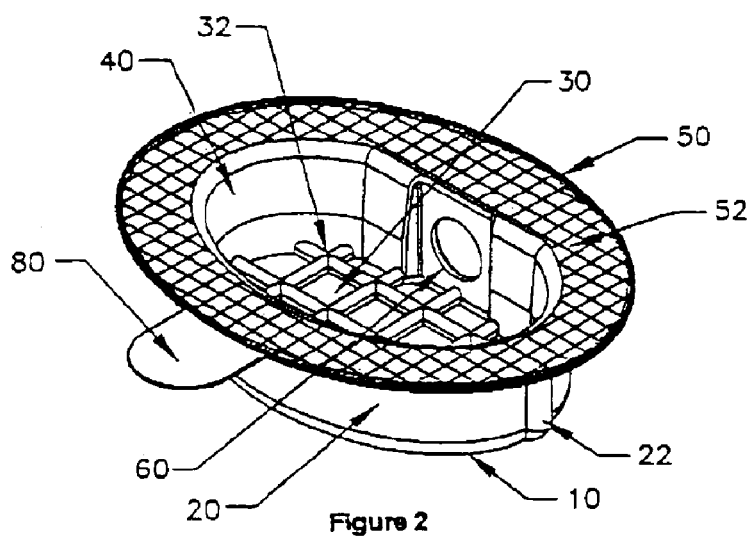
FIG. 2 is an elevated perspective view of the ear coupler in accordance with a preferred embodiment of the present invention, from the opposite side as FIG. 1.
Figure 3:
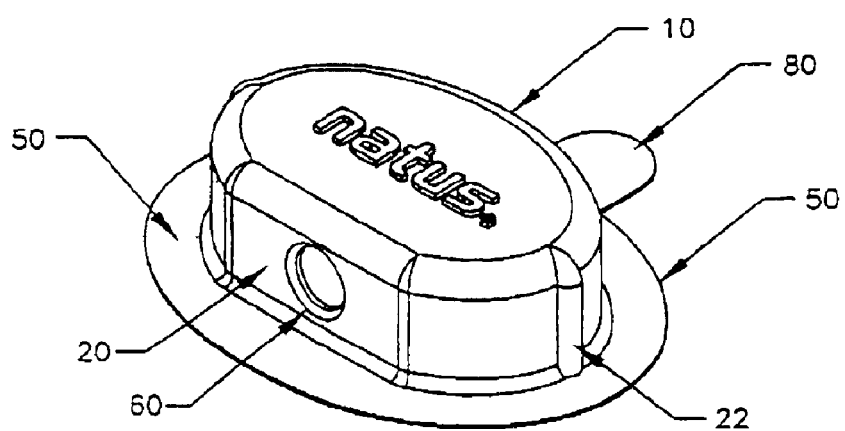
FIG. 3 is a bottom elevated perspective view of the ear coupler in accordance with a preferred embodiment of the present invention.
Figure 4:
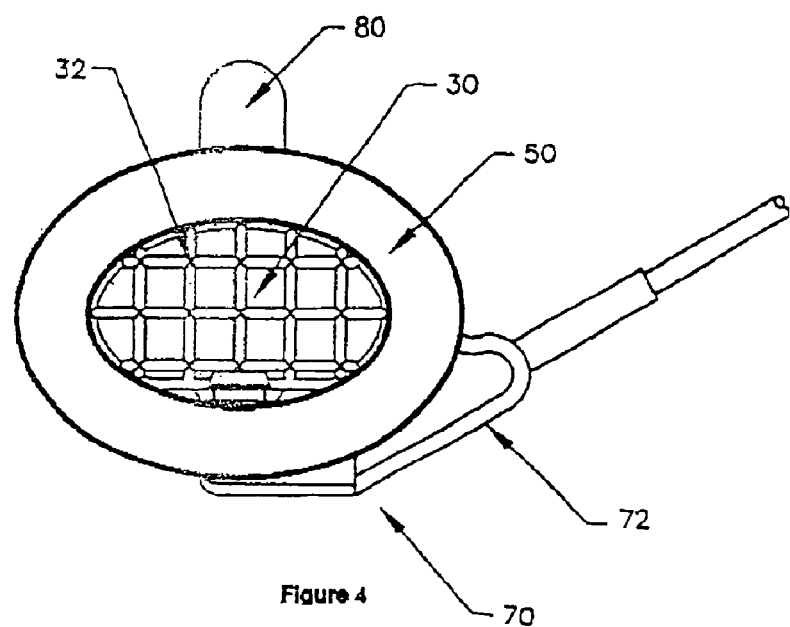
FIG. 4 is a top plan view of the ear coupler in accordance with a preferred embodiment of the present invention, with the ATA.
Figure 5:
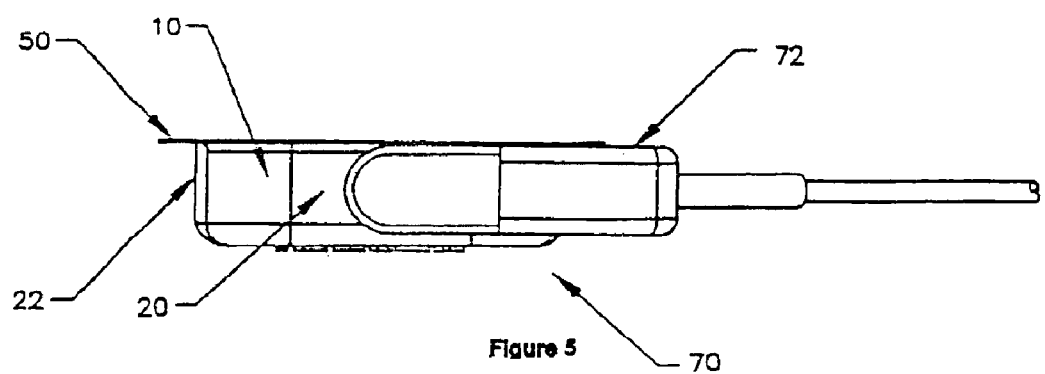
FIG. 5 is a side view of the ear coupler with the ATA in accordance with a preferred embodiment of the present invention.
Figure 6:
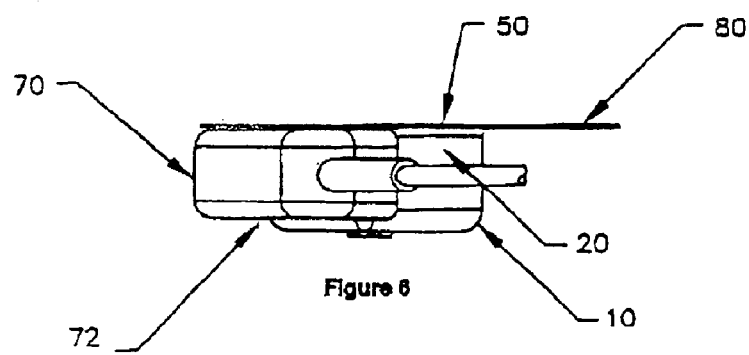
FIG. 6 is a side view, from a different perspective than FIG. 5, of the ear coupler with the ATA in accordance with a preferred embodiment of the present invention.
Figure 7:
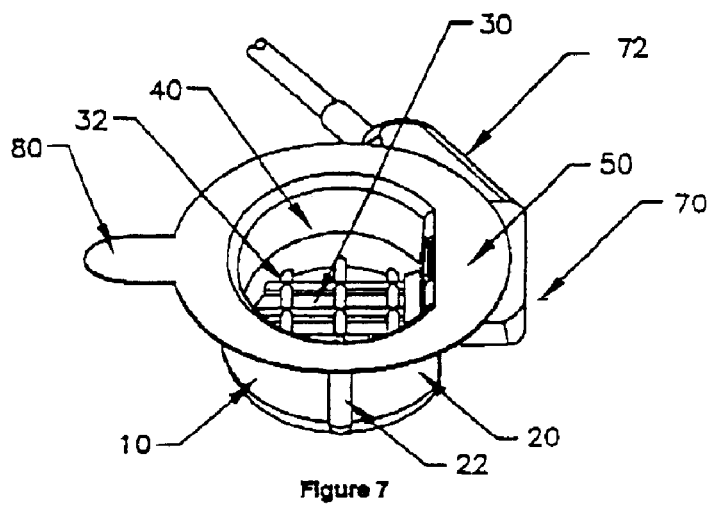
FIG. 7 is an elevated side perspective view of the ear coupler in accordance with a preferred embodiment of the present invention, with the ATA.
Figure 8:
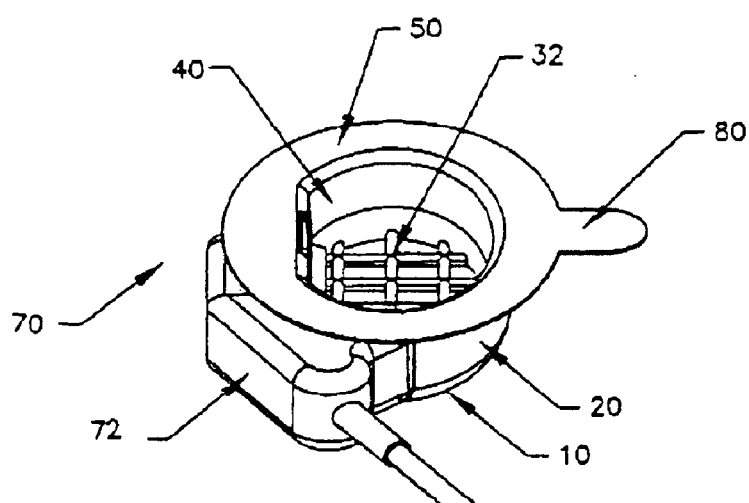
FIG. 8 is an elevated side perspective view of the ear coupler in accordance with a preferred embodiment of the present invention, with the ATA, from the opposite perspective of FIG. 7.
Figure 9:
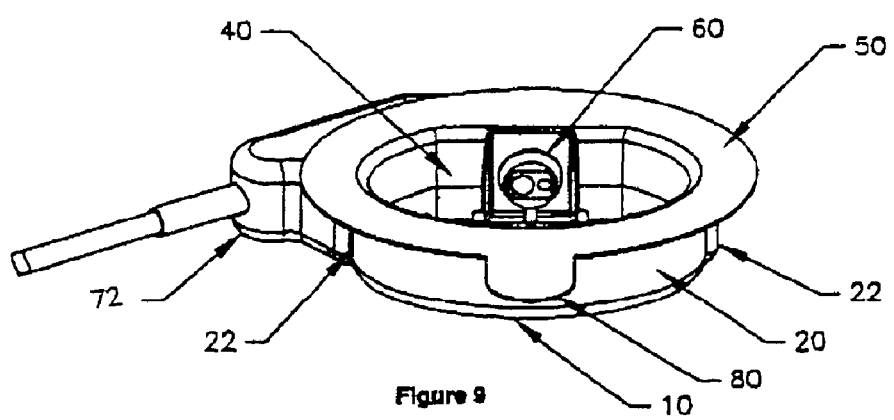
FIG. 9 is an elevated perspective view of the ear coupler in accordance with a preferred embodiment of the present invention, with the ATA.
Figure 10:
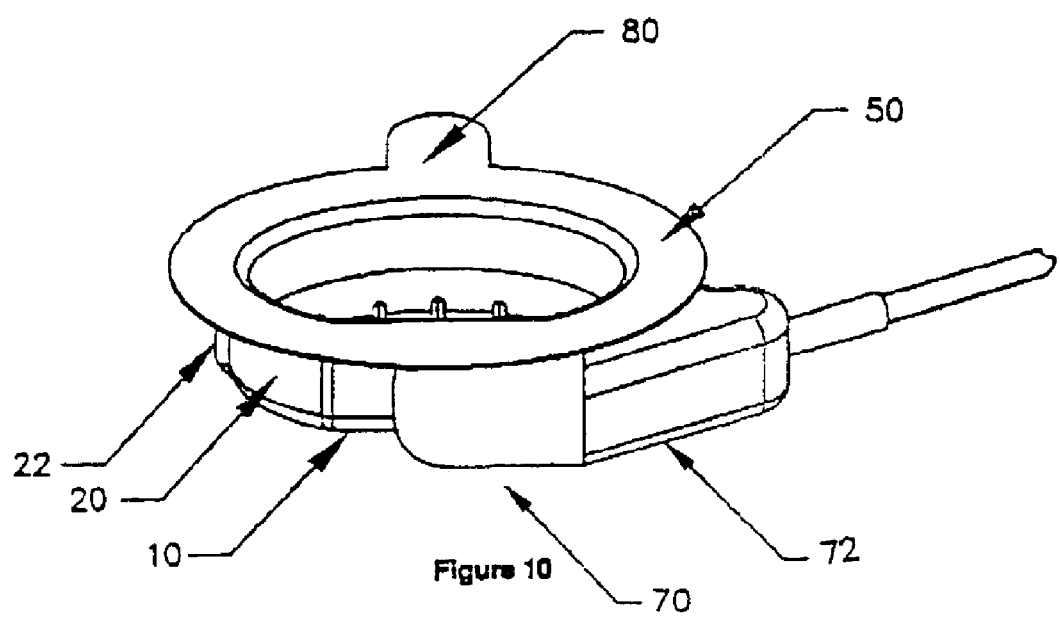
FIG. 10 is an elevated perspective view of the ear coupler in accordance with a preferred embodiment of the present invention, with the ATA, from the opposite perspective of FIG. 9.

The present invention comprises a one-piece, transparent ear coupler body, 10, with an annular side wall, 20, a bottom wall, 30, an internal chamber, 40, a peripheral flange, 50, a port, 60, an ATA, 70, and a tab, 80. Various aspects and features of the preferred embodiment of this invention are described below.

The ear coupler body, 10, is generally D-shaped, and sized to fit an infant's ear. It is made of a flexible, transparent, smooth, non-crumbly, nonporous material, preferably Rimflex®, which is available from Bay State Polymer Distribution, Inc., P.O. Box 40055, Bay Village, Ohio 44140. Other suitable materials include Kraton, PVC, polyurethane, and Engage. By using a transparent material, the ear coupler can be more easily and accurately be placed over the subject's ear. Opaque materials can be used to create the desired acoustic environment, but they do not allow the clinician to visualize the placement of the coupler over the center of the subject's ear.

Preferably, the ear coupler is comprised of one-piece, which may result in lower manufacturing costs compared with multi-piece couplers. However, the coupler can be composed of more than one piece, so long as the pieces or their connections are flexible enough so that ear coupler can accommodate the irregular and curved shape of a subject's head. The ear coupler can be made by injection molding, thermoforming, and other processes. The ear coupler is not "handed," meaning that it can fit on either the right or left ear. The ear coupler is provided clean, and can be sterilized as needed for certain applications. The ear coupler is designed to be disposable.

The annular side wall, 20, forms a ring around the internal portion of the ear coupler. Preferably, the annular side wall forms a D-shaped ring, although other shapes could be used. The D-shape helps to orient placement of the coupler, so that it is placed with the ATA providing the stimulus from the front of the ear. The annular side wall contains two or more ribs, 22, that are used to removably latch the ATA in place, as described below.

The annular side wall should be thick enough to provide crush resistance, and in the preferred embodiment is approximately ⅛th of an inch thick. Ribs, 22, can also be used to improve crush resistance, but in the preferred embodiment, the annular side wall provides sufficient strength on its own. The annular side wall is of uniform thickness, except around the port, 60, where it is substantially thinner in order to help create the interference fit as described below.

The bottom wall, 30, is attached to or integral with the annular side wall. Like the annular side wall, the bottom wall is thick enough to resist crushing when the subject lies on his or her ear. In the preferred embodiment, the bottom wall is approximately ¹⁄₁₆th of an inch thick.

To improve the acoustics of the ear coupler, the surface (exterior or interior) of the bottom wall contains a pattern of surface features, 32. Preferably, these surface features are a pattern of cross-hatched protuberances that create a waffle-type surface. These surface features add strength and rigidity to the bottom wall, and prevent it from vibrating in response to the stimulus. If the bottom wall were subject to vibration, then the ear coupler would create different acoustic environments based on whether the bottom wall was under pressure or not. For instance, if the subject were lying on his or her back, then the bottom wall could vibrate, but if the subject were lying on his or her side, then the ear coupler could be pressed against the bed, thereby inhibiting vibration. By adding the surface features, the ear coupler is not subject to any such vibration regardless of the subject's position, and thus the ear coupler creates the consistent and predictable acoustic environment needed for accurate hearing screening.

The bottom wall also preferably includes a target indicating the center of the coupler, to help facilitate proper placement of the coupler over the subject's ear. The bottom wall could also be imprinted with text, such as the name or trademark of the company manufacturing or selling the ear coupler.

The chamber, 40, is formed by the annular side wall and the bottom wall, and is sufficiently large to accommodate the subject's ear. The chamber creates a tuned, isolated acoustic chamber, with precise acoustic properties so that hearing screening can be conducted. Aural stimuli are transmitted into the chamber through the port.

The flange, 50, extends around the periphery of coupler, projecting out past the annular side wall. The flange may be centered over the internal chamber, or can begin at the annular side wall. The flange can be cut or slit to increase its ability to conform to the subject's head, and indeed, multiple flanges could be used. In the preferred embodiment, as reflected in the drawings, a single unitary flange beginning at the annular side wall is used. The flange should be flexible, so that it can securely attach to the curved and irregular shape of a subject's head.

The flange is relatively planar or smoothly tapered, but may have barriers at the inner and outer periphery to help contain the adhesive. In the preferred embodiment, these barriers take the form of slight ridges that prevent overflow when the flange is coated with adhesive during manufacture.

The preferred adhesive is hydrogel, although other adhesives could be used so long as they allow the coupler to be removably attached to the subject's head. Previous ear couplers have used a laminate for adhesion, which resulted in wasted material, since the adhesive pattern had to be punched from a sheet of hydrogel material. Under the present invention, the hydrogel is selectively applied only to the flange, and then placed on the release paper, resulting in minimal waste.

The flange, coated with adhesive, is the preferred structure to removably attach the ear coupler to the subject's head. However, if a flange is not used, then the ear coupler could be attached to the subject's head by any number of conventional means, such as tape, clips, a headband, or adhesive applied to the periphery of the coupler or to a flexible extension attached to the periphery.

The hydrogel may have a pattern of surface features, 52, on the surface that contacts the infant's head. These surface features may improve adhesion of the flange to the Rimflex®, although they are not present in the preferred embodiment of this invention.

The flange extends from the annular side wall a sufficient distance for proper adhesion. In a preferred embodiment of present invention, the flange extends approximately ¼ inch from the annular side wall.

The port, 60, is an opening in the annular side wall for placement of the ATA, 70. Preferably, the port is sized to create an interference fit with the ATA, so that there is some initial resistance when placing the ATA in the port, and then there is a click or snap when the ATA is pushed into place. For purposes of this patent, "interference fit" denotes the fit between the ATA and the port, whereby there is initial resistance and then relief once the ATA snaps into place. The tip of the ATA is barbed to facilitate insertion into the port. Preferably, when placed on the infant's head, the port will face the front or tragus side of the infant's ear, which corresponds to the flat portion of the "D" shaped coupler.

Figure 11:
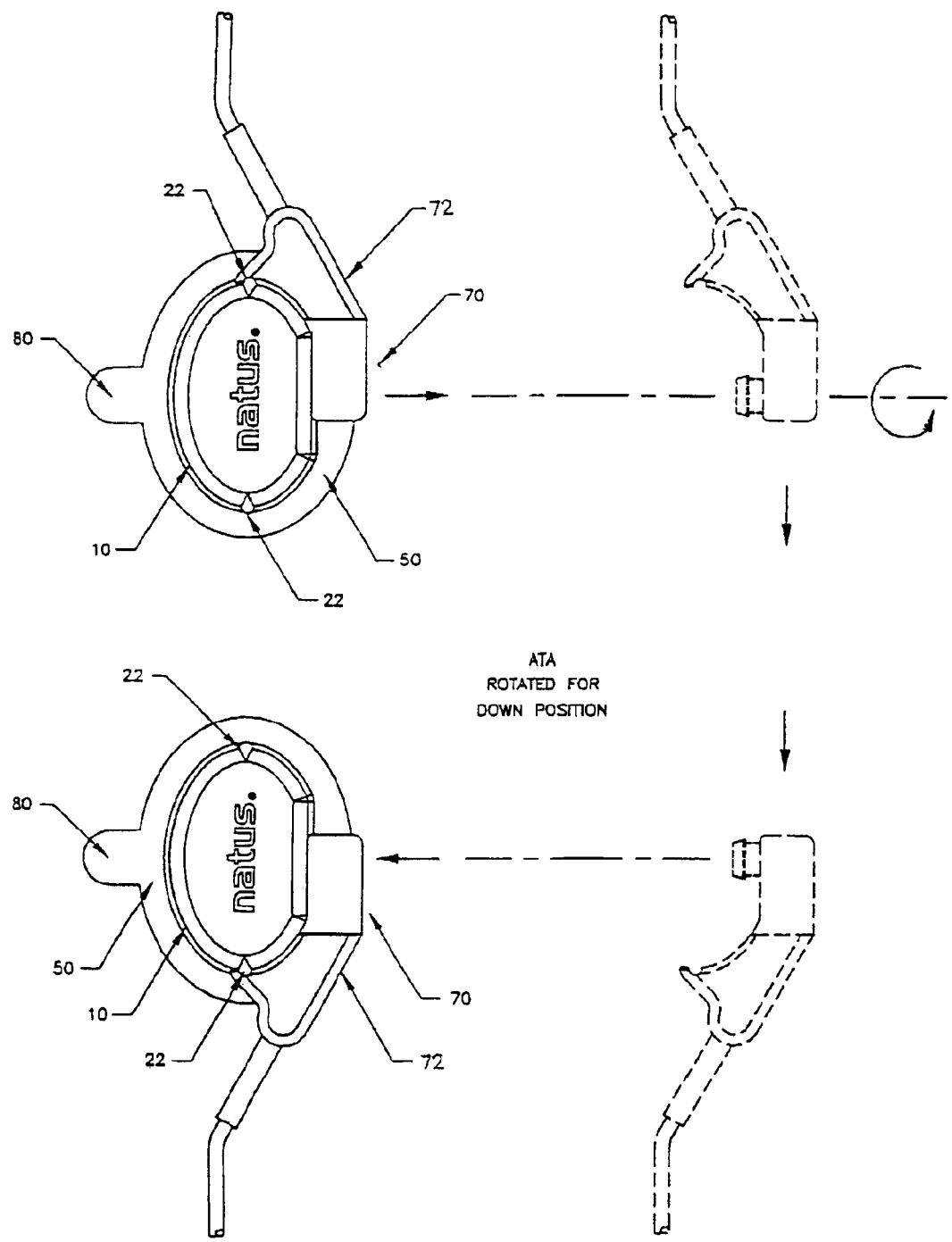
FIG. 11 shows movement of the ATA between the up and down positions.
Figure 12:
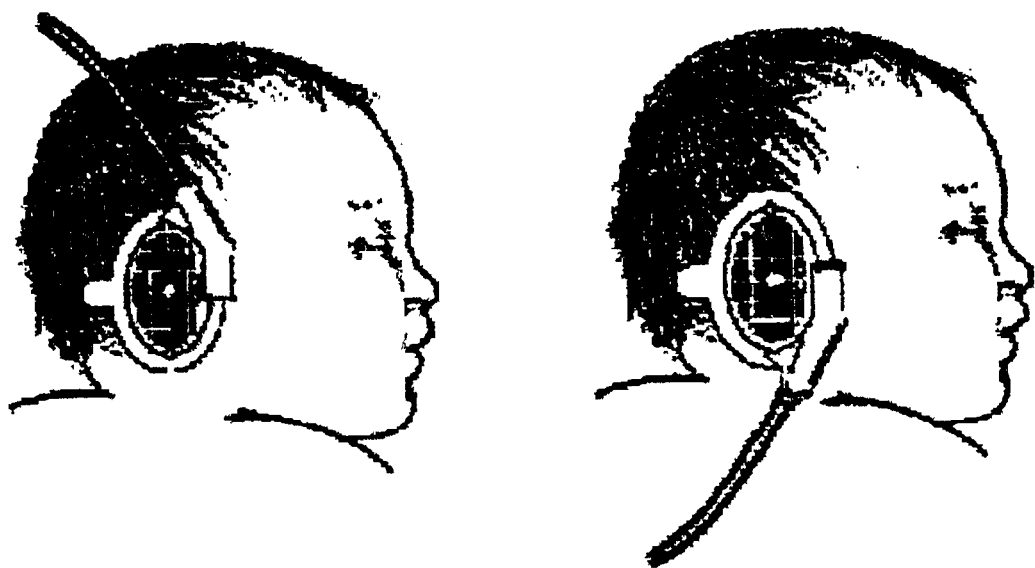
FIG. 12 shows the ear coupler in accordance with a preferred embodiment of the present invention being worn by an infant, with the ATA in both the up and down positions.

The ATA, 70, is an assembly that houses a transducer for generating the aural stimuli. It also may house other devices such as a microphone for monitoring acoustic energy within the environment. The ATA is on the end of a cable, which connects it to the hearing evaluation device. The ATA snaps into the port, and may be positioned in either an up or a down position, along the side of the ear coupler, as illustrated in FIGS. 11 & 12. The ATA can be rotated between the up and down positions during screening, as shown in FIGS. 11 and 12. The ATA also may include a latch that snaps onto the ribs of the annular side wall, helping to ensure that the ear coupler is not tugged away from the subject's head. The ATA hugs or mates with the side of the ear coupler, which improves crush resistance and prevents the ATA from acting as a lever which could pull the ear coupler off the subject's head. More specifically, the ATA has an arm 72 that extends laterally away from the port 60 when the ATA 70 is placed into the port 60. See FIGS. 4, 7, 8, 9, 10, and 11.

The tab, 80, is attached to or integral with the flange, and is used to help remove the ear coupler from the infant's head. Preferably, the tab, 80, is placed opposite to the port, 60, but could be placed anywhere on the periphery of the flange. The tab is also useful in removing the ear coupler from the release paper.

Before use, the ear coupler is provided to the user attached to release paper, to help ensure cleanliness and to preserve the sticking power of the adhesive. Holes may placed in the portion of the release paper facing the bottom wall, to make it easier it to hold the coupler while inserting the ATA.

In operation, the ATA, 70, is inserted into the port, 60, and snapped onto the ribs in either the up or down position, depending on the operator's preference. The ear coupler, 10, is then removed from the release paper and placed on the subject's head, so as to cover his or her ear. The adhesive on the flange, 50, holds the coupler in place during testing. As necessary, the ATA can be flipped from the up or down position during testing to accommodate the particular position of the subject. After testing, the ear coupler is removed, using the tab.

The present ear coupler is much less likely to become detached during testing than previous couplers, since its flexible, one-piece body can better accommodate the irregular and curved shape of the subject's head. It also is better able to move and stretch as necessary in response to the subject's movements.

The present ear coupler is also less costly to manufacture, since it is preferably made of one-piece, and can be created using relatively inexpensive processes such as injection molding and thermoforming.

The ear coupler can be used for hearing screening of infants, children, or adults, and can also be used as a sound-blocking "ear muff," when a quiet acoustic environment is desired.

One skilled in the art will appreciate that the present invention can be practiced by other than the described embodiments, which are presented for purposes of illustration and not limitation. The particular dimensions and materials recited herein are presented for purposes of illustration and not limitation.

We claim:

1. An ear coupler comprising:
   an annular side wall;
   a bottom wall, integral with said annular side wall;
   an internal chamber, formed by said bottom wall and said annular side wall;
   a port in said annular side wall; and
   a highly flexible flange extending from and substantially around said annular side wall.

2. The ear coupler of claim 1, wherein said annular side wall and said bottom wall are transparent.

3. The ear coupler according to claim 1 or 2, additionally comprising ribs in said annular side wall.

4. The ear coupler according to claim 1 or 2, wherein said bottom wall contains surface features.

5. The ear coupler according to claim 1 or 2, wherein said bottom wall contains a target to aid in placing the coupler over the subject's ear.

6. The ear coupler according to claim 1 or 2, wherein said highly flexible flange is coated with adhesive, and wherein said highly flexible flange includes a barrier for containment of said adhesive.

7. The ear coupler according to claim 6, wherein said highly flexible flange additionally includes a second set of surface features to aid in coating said highly flexible flange with said adhesive.

8. The ear coupler according to claim 1 or 2, additionally comprising an acoustic transducer assembly adapted to removably fit in said port.

9. The ear coupler according to claim 8, wherein there is an interference fit between said acoustic transducer assembly and said port.

10. The ear coupler according to claim 9, wherein when said acoustic transducer assembly is fitted in said port, the acoustic transducer assembly mates with the ribs in said annular side wall.

11. The ear coupler according to claim 10, wherein said acoustic transducer assembly can mate in either an up or down position with said ribs in said annular side wall.

12. The ear coupler according to claim 11, wherein said acoustic transducer can be switched between mating positions during use.

13. The ear coupler according to claim 1 or 2, additionally comprising a tab integral with said highly flexible flange.

14. An ear coupler comprising:
    an annular sidewall;
    a bottom wall, integral with said annular side wall;
    an internal chamber, formed by said bottom wall and said annular side wall;
    a port in said annular side wall; and
    a highly flexible flange extending from and substantially around said annular side wall, said flange being coated with adhesive, and having a barrier for containment of said adhesive.

15. An ear coupler comprising a one-piece body, said body having:
    an internal chamber,
    a port in communcation with said chamber,
    a highly flexible flange, coated with adhesive, disposed around said chamber, wherein said body is made by injection molding or thermoforming.

16. The ear coupler according to claim 15, wherein said body is transparent.

17. The ear coupler according to claim 15, additionally comprising a tab integral with said highly flexible flange.

18. The ear coupler according to claim 16, additionally comprising a target to aid in placing the coupler over the subject's ear.

19. An ear coupler comprising:
   an annular side wall;
   a bottom wall, integral with said annular side wall;
   an internal chamber, formed by said bottom wall and said annular side wall;
   a port in said annular side wall for receiving an acoustic transducer assembly, said port sized so as to create an interference fit with said acoustic transducer assembly; and
   a means for removably attaching the ear coupler to a subject's head.

20. An ear coupler comprising:
   an annular side wall;
   a bottom wall, connected with said annular side wall;
   an internal chamber, formed by said bottom wall and said annular side wall;
   a port in said annular side wall; and
   a highly flexible flange connected with and substantially circumscribing said annular side wail, said flexible flange being coated with an adhesive for attaching the ear coupler to a subject's head.

21. An ear coupler comprising:
   an annular side wall;
   a bottom wall, integral with said annular side wall;
   an internal chamber, formed by said bottom wall and said annular side wall;
   a port in said annular side wall; and an acoustic transducer assembly adapted to mate with said annular side wall in an either up or down position.

22. A method for assembling an ear coupler, comprising the steps of:
   providing a one-piece transparent body, said body having an annular side wall, a bottom wall, and a highly flexible flange;
   defining a port for entry of an acoustic transducer assembly in said annular side wall; and dispensing an adhesive on said highly flexible flange.

23. The method according to claim 22, additionally comprising providing for surface features in said bottom wall.

24. The method of claim 23, additionally comprising providing for ribs in said annular side wall.

25. An ear coupler assembly comprising:
   an annular side wall;
   a bottom wall, attached to said annular side wall;
   an internal chamber, formed by said bottom wall and said annular side wall;
   a port in said annular side wall, said port having a longitudinal axis extending into and out of said port; and
   an acoustic transducer assembly capable of being releasably attached to said port so that a portion of said assembly extending from said port is generally perpendicular to said longitudinal axis.

26. A method of preparing an ear coupler for use in hearing evaluation, comprising:
   providing an ear coupler assembly according to claim 25; and
   attaching said acoustic transducer assembly to said port so that a portion of said acoustic transducer assembly is generally perpendicular to said longitudinal axis.

27. An ear coupler assembly comprising:
   an annular side wall;
   a bottom wall, attached to said annular side wall;
   an inernal chamber, formed by said bottom wall and said annular side wall;
   a port in said annular side wall; and
   an acoustic transducer assembly, wherein said acoustic transducer assembly has an arm, and wherein said arm extends laterally away from said port when said acoustic transducer assembly is fitted in said port.

28. A method of preparing an ear coupler for use in hearing evaluation, comprising:
   providing an ear coupler assembly according to claim 27; and
   attaching said acoustic transducer assembly to said port so that said arm extends laterally away from said port.

* * * * *